US006565913B2

(12) United States Patent
Arps et al.

(10) Patent No.: US 6,565,913 B2
(45) Date of Patent: May 20, 2003

(54) NON-IRRITATING ANTIMICROBIAL COATINGS AND PROCESS FOR PREPARING SAME

(75) Inventors: James Arps, San Antonio, TX (US); Geoffrey Dearnaley, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/912,694

(22) Filed: Jul. 24, 2001

(65) Prior Publication Data

US 2003/0031872 A1 Feb. 13, 2003

(51) Int. Cl.⁷ .............................................. C23C 14/02
(52) U.S. Cl. .................... 427/2.24; 427/2.26; 427/525; 427/531; 427/533; 427/537; 427/577; 427/249.7; 427/250; 427/255.7; 204/192.16; 204/192.32
(58) Field of Search ............................. 427/2.24, 2.26, 427/525, 531, 533, 537, 577, 249.7, 250, 255.7; 204/192.16, 192.32

(56) References Cited

U.S. PATENT DOCUMENTS

| 4,241,355 | A | 12/1980 | Bloom et al. |
|---|---|---|---|
| 4,476,590 | A | 10/1984 | Scales et al. |
| 4,615,705 | A | 10/1986 | Scales et al. |
| 4,698,236 | A | 10/1987 | Kellogg et al. |
| 4,718,905 | A | 1/1988 | Freeman |
| 4,906,466 | A | 3/1990 | Edwards et al. |
| 5,079,223 | A | 1/1992 | Maroni |
| 5,192,523 | A | 3/1993 | Wu et al. |
| 5,340,850 | A | 8/1994 | Shimasue |
| 5,352,493 | A | 10/1994 | Dorfman et al. |
| 5,374,318 | A | 12/1994 | Rabalais et al. |
| 5,387,439 | A | 2/1995 | Roberts |
| 5,474,797 | A | 12/1995 | Sioshansi et al. |
| 5,477,864 | A | 12/1995 | Davidson |
| 5,516,884 | A | 5/1996 | Bianconi |
| 5,593,719 | A | 1/1997 | Deanaley et al. |
| 5,605,714 | A | 2/1997 | Deanaley et al. |
| 5,725,573 | A | 3/1998 | Dearnaley et al. |
| 5,753,251 | A | 5/1998 | Burrell et al. |
| 5,770,255 | A | 6/1998 | Burrell et al. |
| 5,780,119 | A | 7/1998 | Dearnaley et al. |
| 5,837,275 | A | 11/1998 | Burrell et al. |
| 5,945,153 | A | * | 8/1999 | Dearnaley .................. 427/2.12 |
| 6,087,025 | A | 7/2000 | Dearnaley et al. |

FOREIGN PATENT DOCUMENTS

| GB | 2287473 | A | 9/1995 |
|---|---|---|---|
| GB | 2287473 | * | 9/1995 |

* cited by examiner

*Primary Examiner*—Timothy Meeks
(74) *Attorney, Agent, or Firm*—Paula D. Morris & Associates, P.C.

(57) ABSTRACT

An adherent antimicrobial coating and method of making same comprising hydrogenated amorphous carbon and a dispersion of antimicrobial metal ions adapted to maintain a therapeutically effective zone of inhibition.

119 Claims, No Drawings

NON-IRRITATING ANTIMICROBIAL COATINGS AND PROCESS FOR PREPARING SAME

FIELD OF THE INVENTION

The present invention provides a coating and a method of making an antimicrobial coating which strongly adheres to surfaces of medical implants and is relatively well-tolerated by the body. When a medical implant bearing the coating is exposed to an solution or alcohol, or is implanted into the body, the coating provides an effective zone of inhibition for a period of about 12 hours or more, preferably for about 24 hours or more, even more preferably for about 3 days or more, and most preferably for about 10 days or more.

BACKGROUND OF THE INVENTION

A common cause of failure of implanted biomedical devices is infection. The attachment of bacteria to medical implants and in-dwelling catheters, and the proliferation of such bacteria, is a major cause of infection during or after the implantation process. Treating an implant with antibiotics has not proven very effective to combat infections, and has sometimes resulted in development of resistant strains of bacteria.

Silver coatings are effective to combat infections; however, contact with a non-leaching silver surface tends to cause tissue irritation. If a coating does leach silver, then the tissue irritation may be somewhat alleviated, but the rate of release of the silver must be controlled. If the silver leaches too slowly, then the coating does not form a zone of inhibition that is effective to prevent infection. If the silver leaches too rapidly, then the zone of inhibition disappears after too short a period of time to prevent infection.

An antimicrobial coating for a medical implant is needed which maintains good adhesion to the implant surface and produces a zone of inhibition that is effective to prevent infection, at least during a sufficient immediate post-operative or post insertion period.

SUMMARY OF THE INVENTION

The invention provides a method of forming an adherent antimicrobial coating on a surface of a substrate, said method comprising:
  exposing said surface to initial conditions effective to convert at least some atoms of said surface to activated atoms;
  condensing a carbonaceous vapor consisting essentially of carbonaceous precursor material onto said surface under condensing conditions effective to induce the formation of covalent bonds between said activated atoms and carbon atoms in said carbonaceous vapor, producing a bonding region comprising hydrogenated amorphous carbon covalently bonded to said substrate;
  exposing an antimicrobial metal to physical vapor deposition techniques, thereby producing a metallic stream consisting essentially of an antimicrobial metal selected from the group consisting of Ag, Au, Pt, Pd, Ir, Sn, Cu, Sb, Bi, Zn, and combinations thereof;
  condensing a combination comprising said carbonaceous vapor and said metallic stream onto said hydrogenated amorphous carbon at a ratio and under incorporation conditions effective to produce an antimicrobial region comprising hydrogenated amorphous carbon having dispersed therein an antimicrobially effective load of antimicrobial metal ions.

The invention also provides a substrate comprising an adherent antimicrobial coating comprising an outer surface, said antimicrobial coating comprising:
  a bonding region immediately adjacent to said substrate consisting essentially of hydrogenated amorphous carbon comprising carbon atoms covalently bonded to atoms in said substrate; and
  an antimicrobial region extending from said bonding region to said outer surface, said antimicrobial region comprising hydrogenated amorphous carbon comprising an antimicrobially effective load of ions of an antimicrobial metal dispersed therein, said antimicrobial metal being selected from the group consisting of Ag, Au, Pt, Pd, Ir, Sn, Cu, Sb, Bi, Zn, and combinations thereof.

DETAILED DESCRIPTION OF THE INVENTION

According to the present invention, a substrate is provided with a film of hydrogenated amorphous carbon in which ions of at least one antimicrobial metal, preferably silver, are disposed. The method used to make the film is ion beam assisted deposition (IBAD).

The ion beam imparts a substantial amount of energy to both the substrate and to the carbonaceous precursor materials as they are deposited onto the substrate. The ion beam activates the substrate so that atoms of the substrate covalently bond with carbon atoms in the carbonaceous precursor material. The result is an interlayer of hydrogenated amorphous carbon comprising carbon atoms covalently bonded to atoms in the substrate. The covalently bonded interlayer prevents delamination of the antimicrobial coating from the substrate surface.

In a preferred embodiment, where the substrate material is a polymer, the covalent bonding comprises carbon-carbon and carbon-hydrogen bonds formed between the carbon in the polymer and the carbon in the hydrogenated amorphous carbon film. In this embodiment. bombardment of the surface of the polymeric component with a beam of energetic ions is believed to disrupt carbon-carbon bonds in the polymer, leaving reactive carbon atoms "dangling" at the surface of the polymer. The carbonaceous precursor material is deposited onto the surface under continued ion bombardment, causing carbon atoms in the precursor material to react with the reactive or "dangling" carbon atoms at the surface of the substrate, thereby forming stable carbon-carbon bonds. The result is a hydrogenated amorphous carbon coating that is bonded to the polymeric substrate by a substantial amount of covalent carbon-carbon bonding.

After the covalently bonded interlayer is produced, a stream of an antimicrobial metal is produced using vapor deposition techniques and introduced essentially simultaneously into the stream of carbonaceous precursor material. Ion bombardment of the combined streams—of carbonaceous precursor material and antimicrobial metal—produces a dispersion of ions of the antimicrobial metal in the hydrogenated amorphous carbon. The form of the dispersion may vary from a substantially uniform dispersion, to a graded dispersion, to actual multilayers of substantially pure hydrogenated amorphous carbon and substantially pure antimicrobial metal. The form of the dispersion depends upon a number of factors, a most important factor being the rate at which the antimicrobial metal is introduced with the stream of carbonaceous precursor material. Preferably, the dispersion is a gradient in which the concentration of antimicrobial metal increases from the covalently bonded interlayer, which consists essentially of hydrogenated amorphous carbon, to the outer surface of the antimicrobial coating. An optional outer film of substantially pure antimicrobial metal also may be deposited.

Suitable Substrates

The antimicrobial coating of the invention is useful on a large variety of substrates, with preferred substrates being those that inherently form covalent bonds with carbon. Most preferred substrates are organic substrates, preferably polymeric substrates. Other suitable substrates include, but are not necessarily limited to metal alloys that have been treated, for example with silicon, to form an outer surface of a material that does covalently bond with carbon.

The antimicrobial coating preferably is applied to the surface of a medical device which comes into contact with alcohol or a water based electrolyte, including a body fluid (for example blood, urine or saliva) or body tissue (for example skin, muscle or bone), for a period of time sufficient for microorganism to grow on the device surface. The term "alcohol or water based electrolyte" also includes alcohol or water based gels. The devices typically are in-dwelling devices (sometimes called medical implants) or other medical devices that contact human tissue during use. Such medical devices include, but are not necessarily limited to catheters, implants, tracheal tubes, orthopedic pins, insulin pumps, wound closures, drains, dressings, shunts, connectors, prosthetic devices, pacemaker leads, needle, surgical instruments, dental prostheses, ventilator tubes and the like. However, the invention is not limited to such devices and may extend to devices useful in consumer healthcare, such as sterile packaging, clothing and footwear, personal hygiene products such as diapers and sanitary pads, biomedical or biotechnical laboratory equipment, such as tables, enclosures, wall coverings, and the like. The term "medical device" as used herein extends broadly to all such devices. The substrate may take on any shape dictated by its utility, ranging from flat sheets to discs, rods to hollow tubes, and the like. The device may be rigid or flexible, a factor again dictated by its intended use.

Where the substrate is an in-dwelling medical device, the substrate preferably is a bioinert material, most preferably a polymeric material. Biocompatible or bioinert materials include, but are not necessarily limited to organic substrates and inorganic substrates. General classes of suitable organic substrates include, but are not necessarily limited to polyethylene, polypropylene, polyurethane, polycarbonates, flourocarbons, and naturally occurring polymers and rubbers. General classes of suitable inorganic substrates include, but are not necessarily limited to silicone, stainless steel, ceramics, metal, and metal alloys.

Examples of organic substrates suitable for application of the film include, but are not necessarily limited to: polyalkylenes, including but not necessarily limited to polyethylenes and polypropylenes, including but not necessarily limited to high density polyethylenes, and ultra-high molecular weight polyethylenes; polyethylene terephthalate; polyetherether ketones; polyether block amides; polyurethanes, including but not necessarily limited to polyetherurethane, polyesterurethane, and other polyurethanes; polyesters; natural rubber; rubber latex; synthetic rubbers; polyester-polyether copolymers; polycarbonates; silicone; polytetraflouroethylene (PTFE); and, other organic materials. Some of these materials are available under various trademarks such as PEBAX™, available from Atochem, Inc. of Glen Rock, N.J.; MYLAR™, available from E. I. duPont deNemours and Co. of Wilmington, Del.; TEXIN™, 985A from Bayer Corporation of Pittsburgh, Pa.; PELLETHANE™, available from Dow Chemical of Midland, Mich.; and LEXAN™, available from General Electric Company of Pittsfield, Mass., and DACRON™ or NYLON™, available from E. I. duPont deNeMours and Co., of Wilmington, Del. Materials that have been approved by the FDA for use in medical implants are preferred materials for use in the present invention.

At least for some inorganic substrates, such as metal alloys, it may be necessary to treat the substrate so that covalent bonds will form between the substrate and the carbon in the carbonaceous precursor material. An example of how a metal alloy substrate may be treated to form covalent bonds with carbon includes, but is not necessarily limited to the method described in U.S. Pat. Nos. 5,593,719; 5,605,714; 5,780,119; 5,725,573; 6,087,025; and 6,171,343, incorporated herein by reference. Using the teachings of these patents to form the present coating on a metal alloy substrate, an interlayer of silicon is formed in a manner effective to form covalent metal-silicide bonds, and to leave an outer film of silicon. The silicon forms covalent bonds with carbon in the carbonaceous precursor material using the present method.

The Hydrogenated Amorphous Carbon

The antimicrobial metal preferably is deposited on the substrate together with a carbonaceous precursor effective to decompose to form hydrogenated amorphous carbon (sometimes herein called "amorphous carbon"). As used herein, the terms "hydrogenated amorphous carbon" or "amorphous carbon" refer to a carbonaceous material composed of a mixture of "$sp^2$" and "$sp^3$" bonded carbon. "$Sp^2$" bonded carbon refers to double bonded carbon commonly associated with graphite. "$Sp^3$" bonded carbon refers to single bonded carbon. Hydrogenated amorphous carbon does not possess a highly ordered crystalline structure, but generally takes the form of small nanometer sized (or larger) islands of graphite dispersed within an amorphous matrix of $Sp^3$ bonded carbon.

Depending upon the method of deposition, the hydrogenated amorphous carbon, may be essentially 100% carbon or may have a sizeable amount (up to 50 atomic %) of C—H bonded hydrogen. Amorphous carbon does not usually exist in bulk form, but is deposited as a coating or film by such methods as ion beam assisted deposition, direct ion beam deposition, magnetron sputtering, ion sputtering, chemical vapor deposition, plasma enhanced chemical vapor deposition, cathodic arc deposition, and pulsed laser deposition.

The Carbonaceous Precursors

Diffusion pump fluids commonly are used as precursor materials for the formation of amorphous carbon. Diffusion pump fluids have a low vapor pressure and can be vaporized stably at room temperature. Examples of diffusion pump fluids which may be modified for use as precursor materials in the present invention include, but are not necessarily limited to: polyphenyl ether; elcosyl naphthalene; i-diamyl phthalate; i-diamyl sebacate; chlorinated hydrocarbons; n-dibutyl phthalate; n-dibutyl sebacate; 2-ethyl hexyl sebacate; 2-ethyl hexyl phthalate; di-2-ethyl-hexyl sebacate; tri-m-cresyl phosphate; tri-p-cresyl phosphate; o-dibenzyl sebacate. Other suitable precursor materials are the vacuum-distilled hydrocarbon mineral oils manufactured by Shell Oil Company under the trademark APIEZON, and siloxanes, such as polydimethyl siloxane, pentaphenyl-trimethyl siloxane, and other silicon containing diffusion pump fluids, preferably pentaphenyl-trimethyl siloxane. Preferred diffusion pump fluids include but are not limited to, polyphenyl ether and elcosyl naphthalene. A most preferred carbonaceous precursor is polyphenyl ether. Polydimethyl siloxane, pentaphenyl-triethyl siloxane, and other silicon containing diffusion pump fluids will work in the present invention, but are not preferred where the silicon contained in these diffusion pump fluids may be a component of the outer coating of the implant. Other suitable carbonaceous precursors contain carbon and other constituent elements, such as oxygen, nitrogen, or fluorine.

The carbonaceous precursor material is vaporized, and the "carbonaceous vapor" is condensed onto the surface of the components using known means. Generally the precursor is placed in a reservoir, heated to vaporization, typically between about 150° C.–185° C. (320° F.–365° F.), and directed onto the component, for example, using a right angled nozzle. Either substantially simultaneously or sequentially, the component is bombarded, either in a continuous or interrupted fashion, with an energetic beam of ions. Preferably, the bombardment is substantially simultaneous with vapor deposition of the precursor material. The ions preferably are ionized gaseous species such as hydrogen, helium, neon, nitrogen, argon, methane, carbon monoxide, or other relatively low mass gaseous elements or compounds. Preferred ions are selected from the group consisting of nitrogen ions and argon ions. The ion beam has an energy between about 500 eV to 100 keV, preferably from about 1 keV about 10 keV, most preferably about 3 keV. The energy of bombardment is sufficient to ionize the constituent molecules in the precursor film, and to rupture the bonds between hydrogen and other atoms, thereby releasing the hydrogen into the surrounding vacuum to be pumped away.

After a sufficient amount of time has passed to form a "bonding region" consisting essentially of hydrogenated amorphous carbon, a "metallic stream" of the antimicrobial metal is introduced.

The Antimicrobial Metal

Suitable "antimicrobial metals" for use in producing the coating include, but are not necessarily limited to Ag, Au, Pt, Pd, Ir, Sn, Cu, Sb, Bi, and Zn, and combinations thereof. Preferred antimicrobial metals include, but are not necessarily limited to Ag and Au. A most preferred antimicrobial metal is Ag.

A "metallic stream" may be deposited onto the surface of the implant in several different ways. Preferred methods are known as physical vapor deposition techniques. Physical vapor deposition techniques deposit the metal from a vapor, generally atom by atom, onto a substrate surface. The techniques include, but are not necessarily limited to vacuum or arc evaporation, thermal vapor deposition, sputtering, and magnetron sputtering.

In a first method, a vaporized stream of the metal is directed toward the surface to be treated via a sputtering process. In this embodiment, the rate of arrival of the metal ions may be controlled directly by controlling the intensity of the ion beam measured as an electrical current to the sputtering electrode. In other methods, the vaporized steam of the metal is generated from a pool of metal in an electron beam heated hearth, or from a pool of molten metal contained in a resistively heated evaporator. The vaporization of silver generally takes place at a temperature of approximately 1000° C., and the rate of arrival of the metal may be controlled by controlling the thermal power delivered to the hearth or the evaporator. In another method, described in more detail below, the metal is provided in an organometallic compound that is used as the carbonaceous precursor for the DLC coating.

Ion Beam Assisted Deposition

In order to form an antimicrobial coating that adheres strongly to the substrate, standard wet chemical treatments are first performed. The substrate surface is then sputter cleaned with a beam of ions, preferably argon and/or nitrogen ions. The sputtering is continued for a period of time effective to remove superficial contaminants and grease, and the sputtering takes place at an energy and a power density effective to activate atoms of the substrate at the surface. The activated atoms forms covalent bonds with carbon atoms in the carbonaceous precursor material.

Where the substrate is polymeric, the substrate is bombarded for about 2 minutes to about 30 minutes with a beam of ions at from about 0.05 to about 10 keV and from about 5 to about 50 mA. Preferably, the ion beam is continued while a "carbonaceous vapor" consisting essentially of the selected carbonaceous precursor is introduced and directed onto the surface of the substrate. The ion beam decomposes the carbonaceous precursor substantially as it condenses on the surface of the substrate. The process is continued until a layer of hydrogenated amorphous carbon of about 0.05 micron to about 0.5 micron is formed. The substrate temperature during deposition of the carbonaceous vapor is sufficiently low to avoid damaging the substrate and to allow the carbonaceous vapor to condense onto the substrate surface. Typically, the substrate temperature is from about 25° C. to about 125° C.

Thereafter, a metallic stream consisting essentially of the antimicrobial metal, preferably silver, is introduced at a predetermined rate using vapor deposition techniques, discussed above. Where the antimicrobial metal is silver, the total quantity of silver required for the final coating to be antimicrobial effective is from about 0.05 to about 1 mg/cm$^2$, preferably about 0.1 mg/cm$^2$ based on the surface area of the coating. In order to form an antimicrobial coating with a graded silver content, a silver stream is introduced at from about 0.5 Å/second to about 1 Å/second for about 15 to about 30 minutes, as measured by a quartz crystal microbalance. The rate of silver introduction is then increased to from about 2 Å/second to about 5 Å/second for about 15 to about 30 minutes. Depending upon the total quantity of silver desired, the rate of silver introduction is increased up to about 10 Å/second, with each gradient taking from about 15 to about 30 seconds to form. The result is an antimicrobial coating, preferably having a thickness of from about 0.01 microns to about 5 microns, preferably about 0.05 microns, and having a distribution of silver of from about 0% to about 100%, depending upon the rate of introduction of silver at any particular point in the process. If desired, an outer surface of substantially pure silver is produced by simply discontinuing the flow of the carbonaceous vapor while maintaining the flow of the silver vapor, with or without the ion beam.

The "ion arrival ratio" is controlled in relation to the rate of arrival of the carbonaceous precursor molecules. The "ion arrival ratio" is the ratio of each arriving ion to the number of precursor molecules present at the surface of the component. The ion arrival ratio preferably is at least 1 ion for every molecule of carbonaceous precursor. This process requires about one ion for every 100 atoms in the final product coating; however, the required ion-to-atom ratio will vary according to the mass and energy of the ion species. Typically, 100 eV must be deposited for each carbon atom in the coating.

The function of this ion bombardment step is to rupture at least about 80% of the is carbon-hydrogen bonds in the precursor, resulting in the formation of a noncrystalline coating of hydrogenated amorphous carbon. The energy dissipated by the energetic ion bombardment during ion beam assisted deposition is in the form of inelastic electronic excitations equivalent to at least about 100 eV for each carbon atom within the deposited coating. This energy dissipation strongly enhances adhesion of the DLC coating by rupturing and subsequently reforming interatomic bonds across the interfaces. Persons of ordinary skill in the art will recognize how to achieve the current linear energy of transfer in the ionizing process.

The coating is formed on at least a part of the surface of the medical device. The film has a thickness no greater than that needed to provide release of metal ions on a sustainable basis over a suitable period of time. In that respect, the thickness varies with the particular metal in the coating (which varies the solubility and abrasion resistance), and with the solubility of the metal. The thickness is thin enough that the coating does not interfere with the dimensional tolerances or flexibility of the device for its intended utility. Typically, coating thicknesses of about 3 microns or less, preferably about 1 micron or less, most preferably less than 1 micron provide an effective zone of inhibition. Increased thicknesses may be used depending on the degree of metal ion release needed over a period of time. Thicknesses greater than 10 microns are more expensive to produce and normally are not needed.

The Zone of Inhibition

Upon implantation into the body, the metal ions "leach" from the antimicrobial coating. Without limiting the invention to a particular mechanism of action, electrochemical repulsion is believed to force the positively charged, relatively conductive antimicrobial metal ions from the relatively inert, non-conductive hydrogenated amorphous carbon and into the surrounding alcohol or water based electrolyte. The rate of leaching is believed to be substantially proportional to the concentration of silver in the portion of the coating from which the silver is being leached.

The result is an "effective zone of inhibition" comprising a zone of a therapeutically active level of the antimicrobial metal ions. The zone of inhibition remains therapeutically active for at least about 12 hours, preferably for at least about 24 hours, more preferably for at least about 3 days, and most preferably for at least about 10 days. In the laboratory, the antimicrobial coatings release antimicrobial metal ions into an alcohol or water based electrolyte on a sustainable basis during the therapeutically active period.

The term "sustainable basis" is used to differentiate the rate of release of the antimicrobial metal ions from the DLC coating versus the rate of release of the antimicrobial metal ions from bulk metal. Bulk metals generally are "non-leaching," which means that bulk metals release metal ions at a rate and concentration which is too low to achieve an antimicrobial effect. In contrast, highly soluble salts, such as silver nitrate, release silver ions virtually instantly upon contact with an alcohol or water based electrolyte. The coatings of the present invention release antimicrobial metal ions at a sufficient rate and concentration, over a sufficient period of time to provide an "effective zone of inhibition."

As used herein, the term "effective zone of inhibition" means that ions of the anti-microbial metal are released from the coating into an electrolyte in contact with the coating in a concentration sufficient to inhibit bacterial growth in the vicinity of the coating, or in a "zone of inhibition" (ZOI) with respect to the coating. The ZOI is measured by placing the coating or material on a bacterial "lawn." A relatively small or no ZOI (ex. less than 1 mm) indicates an ineffective zone of inhibition. A larger ZOI (ex. 3 mm or greater, preferably 5 mm or greater) indicates an effective zone of inhibition. One procedure for a ZOI test is described in the Examples. The antimicrobial coatings of the present invention exhibit an effective zone of inhibition of 1 mm or more, preferably 2 mm or more, even more preferably 3 mm or more. The effective zone of inhibition is maintained for a period of time at least sufficient to prevent post operative infection. The time period required to prevent post operative infection may vary depending upon the device involved. For example, where the coating is on a catheter, the time period required for an effective zone of inhibition may be as short as about 12 hours or more, preferably about 3 days or more. Where the coating is on an indwelling device, an effective ZOI is maintained for at least about 12 hours, preferably at least about 24 hours, more preferably about 3 days or more, even more preferably about 10 days or more.

The anti-microbial effect of the coating is achieved when the device is brought into contact with an alcohol or a water based electrolyte, such as a body fluid or body tissue, thus releasing the antimicrobial metal ions. The concentration of the metal which is needed to produce an anti-microbial effect will vary from metal to metal. Generally, anti-microbial effect is achieved in body fluids such as plasma, serum or urine at metal ion concentrations of about 0.5–1.5 $\mu$g/ml or less.

The rate of release of antimicrobial metal ions from a coating on a sustainable basis is dictated by a number of factors. These factors include, but are not necessarily limited to the composition of the coating, the solubility of the antimicrobial metal ions, the thickness of the coating, the concentration of antimicrobial metal ions at any given point, and the nature of the environment in which the device is used. The metal ions nearest the surface of the coating leach from the coating first. The rate of release of metal ions at any given time is proportional to the concentration of metal ions at the depth of the coating from which the metal ions are being leached. As the level of antimicrobial metal ions at the depth of the coating from which the silver is leaching increases, the amount of metal ions released from the coating per unit time increases. Alteration of the gradient and concentration of the antimicrobial metal in the coating provides a method which may be adapted to produce controlled release of the antimicrobial metal ions.

The invention will be better understood with reference to the following examples which are illustrative only:

EXAMPLE 1

Initial tests were conducted to assess the importance of an interlayer of hydrogenated amorphous carbon on adherence of coatings containing silver ions formed on a polypropylene sheet material.

The polypropylene substrate is bombarded for about 15 minutes with a 3 keV, 12 mA nitrogen ion beam. The ion beam was continued while a vapor of polyphenyl ether was introduced for the period of time specified in the following Table. The substrate temperature was maintained at about 50° C. Thereafter, a vaporized stream of silver was introduced at the rate and for the period of time specified in the following Table:

| Candidate | Material Deposited | Time |
|---|---|---|
| 1 | Carbonaceous precursor | 2 minutes |
|   | Carbonaceous precursor and silver | 156 minutes |
| 2 | Carbonaceous precursor | 15 minutes |
|   | Carbonaceous precursor + Ag (0.5 Å/sec) | 10 minutes |
|   | Carbonaceous precursor + Ag (1 Å/sec) | 5 minutes |
|   | pure silver (5 Å/sec) | 5 minutes |
| 3 | non-IBAD: pure silver (approximately 1000 to 2000 Å thick) | 20 minutes |
| 4 | Carbonaceous precursor | 40 minutes |
| 5 | Carbonaceous precursor + 20% Ag | 20 minutes |
|   | Ag (2 Å/sec) | 10 minutes |
|   | Carbonaceous precursor | 20 minutes |
| 6 | Ag (2 Å/sec) | 10 minutes |
| 7 | Carbonaceous precursor | 15 minutes |
|   | Subst. uniform Ag/Amorphous Carbon | 30 minutes |
| 8 | Carbonaceous precursor | 15 minutes |
|   | Graded Ag/Carbonaceous precursor | 30 minutes |
| 9 | Pure Ag (2 Å/sec) | 10 minutes |
| 10 | Pure carbonaceous precursor | 15 minutes |

The adherence of the coatings was evaluated by SEM at low and high magnifications to determine the extent of coating integrity following coating deposition, as well as any coating defects or uncoated regions. The samples were cut to size with scissors. Regions at the cut edge, as well as the center of the 1 in.×1 in. sample were analyzed for coating In general, coating uniformity was good. Candidate 3 (non-IBAD Ag) showed extremely poor adherence. Extensive coating delamination and flaking of the Candidate 3 (Ag) coating were observed. Adherence of the DLC coating (Candidate 4) was good. The combined Ag/DLC coatings (Candidates 1, 2, 4, 7, and 8) showed significant improvement in adherence relative to the Ag coating. Delamination and flaking were not detected for the Ag/DLC samples evaluated. Some craze lines were observed near fold lines on Candidate 1. The graded DLC/Ag coating (Candidate 2) did not exhibit as much crazing, and adherence of Candidate 2 was good. The performance demonstrated that an interlayer of hydrogenated amorphous carbon improves adhesion of the coating to polypropylene.

EXAMPLE 3

Magnetron sputtering of the silver was investigated as an alternative to thermal vapor deposition. A number of graded coatings were successfully applied to polypropylene using magnetron sputtering of the silver instead of thermal vaporization. Magnetron sputtering may be a preferred method for scaled up coating preparation.

EXAMPLE IV

Samples of polypropylene bearing a coating similar to that of Candidate 2 were tested to assess their production of a zone of inhibition (ZOI) using the Kirby-Bauer Standard Antimicrobial Susceptibility test. The results are shown in the following Table:

| ORGANISM (strain) | Day #1-zone diameters (mm) (mean =/− SD) | Day #2-zone diameters (mm) (mean =/− SD) |
|---|---|---|
| *Klebsiella pneumonaie* (ATCC 13883) | 4.4 +/− 0.1 | 0.0 +/− 0.0 |
| *Strenothopho-monas malthophillia* (ATCC 13637) | 5.6 +/− 0.5 | 0.0 +/− 0.0 |
| *Staphylococcus aureus* (ATCC 29213) | 4.2 +/− 0.3 | 0.9 +/− 1.4 |
| *Escherichia coli* (ATCC 35150) H157:07 | 5.1 +/− 0.3 | 1.1 +/− 1.7 |
| *Escherichia coli* (ATCC 25922) | 5.4 +/− 0.5 | 2.6 +/− 1.5 |
| *Psuedomonas aeruginosa* (ATCC27853) | 5.1 +/− 0.7 | 1.2 +/− 1.8 |
| *Enterococcus faecalis* (ATCC51299) VRE | 4.5 +/− 0.2 | 0.0 +/− 0.0 |
| *Staphylococcus aureus* (CPCM-^) | 4.0 +/− 0.3 | 0.0 +/− 0.0 |
| *Staphylococcus epidermidis* (ATCC 12228) | 5.9 +/− 0.5 | 2.8 +/− 1.6 |

*modified Kirby-Bauer Method

Many modifications and variations may be made in the embodiments described herein and depicted in the accompanying drawings without departing from the concept of the present invention. Accordingly, it is clearly understood that the embodiments described and illustrated herein are illustrative only and are not intended as a limitation upon the scope of the present invention.

We claim:

1. A method of forming an adherent antimicrobial coating on a surface of a substrate, said method comprising:

exposing said surface to initial conditions effective to convert at least some atoms of said surface to activated atoms;

condensing a carbonaceous vapor consisting essentially of carbonaceous precursor material onto said surface under condensing conditions effective to induce the formation of covalent bonds between said activated atoms and carbon atoms in said carbonaceous vapor, producing a bonding region comprising hydrogenated amorphous carbon covalently bonded to said substrate;

exposing an antimicrobial metal to physical vapor deposition techniques, thereby producing a metallic stream consisting essentially of an antimicrobial metal selected from the group consisting of Ag, Au, Pt, Pd, Ir, Sn, Cu, Sb, Bi, Zn, and combinations thereof;

condensing a combination comprising said carbonaceous vapor and said metallic stream onto said hydrogenated amorphous carbon at a ratio and under incorporation conditions effective to produce an antimicrobial region comprising hydrogenated amorphous carbon having dispersed therein an antimicrobially effective load of antimicrobial metal ions.

2. The method of claim 1 wherein said condensation conditions comprise bombardment with a beam of ions at an condensation energy and amperage effective to induce said formation of covalent bonds and to convert said carbonaceous precursor material to said hydrogenated amorphous carbon; and said incorporation conditions comprise bombardment with a beam of ions at an incorporation energy and amperage effective to convert said combination to hydrogenated amorphous carbon having dispersed therein an antimicrobially effective load of antimicrobial metal ions.

3. The method of claim 2 wherein both said condensation energy and amperage and said incorporation energy and amperage have the following values:
said energy is from about 1 to about 10 keV; and,
said amperage is from about 10 to about 50 mA.

4. The method of claim 3 wherein said antimicrobial metal is selected from the group consisting of Au and Ag.

5. The method of claim 4 wherein said metallic stream is introduced at a varied rate effective to produce said load of from about 0.5 to about 1 mg/cm$^2$ based on surface area of the coating.

6. The method of claim 5 wherein said varied rate is from about 0.5 Å/sec to about 10 Å/sec.

7. The method of claim 5 wherein said varied rate comprises
an initial rate of from about 0.5 Å/sec to about 10 Å/sec; and
a subsequent rate of from about 2 Å/sec to about 5 Å/sec.

8. The method of claim 7 wherein said initial rate and said subsequent rate each are maintained for about 15 minutes to about 30 minutes.

9. The method of claim 3 wherein said metallic stream is introduced at a varied rate effective to produce said load of from about from about 0.5 to about 1 mg/cm$^2$ based on surface area of the coating.

10. The method of claim 9 wherein said varied rate is from about 0.5 Å/sec to about 10 Å/sec.

11. The method of claim 10 wherein said varied rate comprises
an initial rate of from about 0.5 Å/sec to about 10 Å/sec; and
a subsequent rate of from about 2 Å/sec to about 5 Å/sec.

12. The method of claim 11 wherein said initial rate and said subsequent rate each are maintained for about 15 minutes to about 30 minutes.

13. The method of claim 3 further comprising discontinuing said carbonaceous vapor to produce an antimicrobial coating comprising an outer surface consisting essentially of said antimicrobial metal.

14. The method of claim 2 wherein said antimicrobial metal is selected from the group consisting of Au and Ag.

15. The method of claim 2 wherein said metallic stream is introduced at a varied rate effective to produce said load of from about from about 0.5 to about 1 mg/cm$^2$ based on surface area of the coating.

16. The method of claim 15 wherein said varied rate is from about 0.5 Å/sec to about 10 Å/sec.

17. The method of claim 15 wherein said varied rate comprises
an initial rate of from about 0.5 Å/sec to about 10 Å/sec; and
a subsequent rate of from about 2 Å/sec to about 5 Å/sec.

18. The method of claim 17 wherein said initial rate and said subsequent rate each are maintained for about 15 minutes to about 30 minutes.

19. The method of claim 14 wherein said metallic stream is introduced at a varied rate effective to produce said load of from about 0.5 to about 1 mg/cm$^2$ based on surface area of the coating.

20. The method of claim 19 wherein said varied rate is from about 0.5 Å/sec to about 10 Å/sec.

21. The method of claim 19 wherein said varied rate comprises
an initial rate of from about 0.5 Å/sec to about 10 Å/sec; and
a subsequent rate of from about 2 Å/sec to about 5 Å/sec.

22. The method of claim 21 wherein said initial rate and said subsequent rate each are maintained for about 15 minutes to about 30 minutes.

23. The method of claim 2 further comprising discontinuing said carbonaceous vapor to produce an antimicrobial coating comprising an outer surface consisting essentially of said antimicrobial metal.

24. The method of claim 1 wherein said antimicrobial metal is selected from the group consisting of Au and Ag.

25. The method of claim 24 wherein said metallic stream is introduced at a varied rate effective to produce said load of from about 0.5 to about 1 mg/cm$^2$ based on surface area of the coating.

26. The method of claim 25 wherein said varied rate is from about 0.5 Å/sec to about 10 Å/sec.

27. The method of claim 25 wherein said varied rate comprises
an initial rate of from about 0.5 Å/sec to about 10 Å/sec; and
a subsequent rate of from about 2 Å/sec to about 5 Å/sec.

28. The method of claim 27 wherein said initial rate and said subsequent rate each are maintained for about 15 minutes to about 30 minutes.

29. The method of claim 1 wherein said metallic stream is introduced at a varied rate effective to produce said load of from about 0.5 to about 1 mg/cm$^2$ based on surface area of the coating.

30. The method of claim 29 wherein said varied rate is from about 0.5 Å/sec to about 10 Å/sec.

31. The method of claim 30 wherein said varied rate comprises
an initial rate of from about 0.5 Å/sec to about 10 Å/sec; and
a subsequent rate of from about 2 Å/sec to about 5 Å/sec.

32. The method of claim 31 wherein said initial rate and said subsequent rate each are maintained for about 15 minutes to about 30 minutes.

33. The method of claim 1 further comprising discontinuing said carbonaceous vapor to produce an antimicrobial coating comprising an outer surface consisting essentially of said antimicrobial metal.

34. A method of forming an adherent antimicrobial coating on a surface of a substrate, said method comprising:
exposing said surface to initial conditions effective to convert at least some atoms of said surface to activated atoms;
condensing a carbonaceous vapor consisting essentially of carbonaceous precursor material onto said surface under condensing conditions effective to induce the formation of covalent bonds between said activated atoms and carbon atoms in said carbonaceous vapor, producing a bonding region comprising hydrogenated amorphous carbon covalently bonded to said substrate;
exposing silver to physical vapor deposition techniques, thereby producing a metallic stream consisting essentially of silver;
condensing a combination comprising said carbonaceous vapor and said metallic stream onto said hydrogenated amorphous carbon at a ratio and under incorporation conditions effective to produce an antimicrobial region comprising hydrogenated amorphous carbon having dispersed therein an antimicrobially effective amount of silver ions.

35. The method of claim 34 wherein
said condensation conditions comprise bombardment with a beam of ions at an condensation energy and amperage effective to induce said formation of covalent bonds and to convert said carbonaceous precursor material to said hydrogenated amorphous carbon; and said incorporation conditions comprise bombardment with a beam of ions at an incorporation energy and amperage effective to convert said combination to hydrogenated amorphous carbon having dispersed therein an antimicrobially effective amount of antimicrobial metal ions.

36. The method of claim 35 wherein both said condensation energy and amperage and said incorporation energy and amperage have the following values:

said energy is from about 1 to about 10 keV; and, said amperage is from about 10 to about 50 mA.

37. The method of claim 36 wherein said metallic stream is introduced at a varied rate effective to incorporate a final concentration of antimicrobial metal in said coating of from about from about 0.5 to about 1 mg/cm² based on surface area of the coating.

38. The method of claim 37 wherein said varied rate is from about 0.5 Å/sec to about 10 Å/sec.

39. The method of claim 37 wherein said varied rate comprises an initial rate of from about 0.5 Å/sec to about 10 Å/sec; and a subsequent rate of from about 2 Å/sec to about 5 Å/sec.

40. The method of claim 39 wherein said initial rate and said subsequent rate each are maintained for about 15 minutes to about 30 minutes.

41. The method of claim 35 wherein said metallic stream is introduced at a varied rate effective to incorporate a final concentration of antimicrobial metal in said coating of from about from about 0.5 to about 1 mg/cm based on surface area of the coating.

42. The method of claim 41 wherein said varied rate is from about 0.5 Å/sec to about 10 Å/sec.

43. The method of claim 41 wherein said varied rate comprises an initial rate of from about 0.5 Å/sec to about 10 Å/sec; and a subsequent rate of from about 2 Å/sec to about 5 Å/sec.

44. The method of claim 43 wherein said initial rate and said subsequent rate each are maintained for about 15 minutes to about 30 minutes.

45. The method of claim 34 wherein said metallic stream is introduced at a varied rate effective to incorporate a final concentration of antimicrobial metal in said coating of from about from about 0.5 to about 1 mg/cm² based on surface area of the coating.

46. The method of claim 45 wherein said varied rate is from about 0.5 Å/sec to about 10 Å/sec.

47. The method of claim 45 wherein said varied rate comprises an initial rate of from about 0.5 Å/sec to about 10 Å/sec; and a subsequent rate of from about 2 Å/sec to about 5 Å/sec.

48. The method of claim 47 wherein said initial rate and said subsequent rate each are maintained for about 15 minutes to about 30 minutes.

49. A method of forming an adherent antimicrobial coating on a surface of a substrate, said method comprising:

bombarding said surface with a beam of ions under conditions effective to convert at least some surface atoms to activated atoms;

directing a carbonaceous vapor consisting essentially of carbonaceous precursor material onto said surface under conditions effective to condense said carbonaceous vapor onto said surface and to induce at least a quantity of carbon atoms in said carbonaceous vapor to covalently bond with said activated atoms and to produce a bonding region consisting essentially of hydrogenated amorphous carbon covalently bonded to said surface;

producing a metallic stream consisting essentially of silver using physical vapor deposition techniques;

introducing said metallic stream into said carbonaceous vapor, producing a combined stream;

condensing said combined stream onto said bonding region; and, bombarding said combined stream on said bonding region under conditions effective to form an antimicrobial region comprising an antimicrobially effective amount of silver ions dispersed in hydrogenated amorphous carbon.

50. The method of claim 19 wherein said metallic stream is introduced at a varied rate effective to incorporate a final concentration of silver in said coating of from about from about 0.5 to about 1 mg/cm² based on surface area of the coating.

51. The method of claim 50 wherein said varied rate is from about 0.5 Å/sec to about 10 Å/sec.

52. The method of claim 50 wherein said varied rate comprises an initial rate of from about 0.5 Å/sec to about 10 Å/sec; and a subsequent rate of from about 2 Å/sec to about 5 Å/sec.

53. The method of claim 52 wherein said initial rate and said subsequent rate each are maintained for about 15 minutes to about 30 minutes.

54. A method of forming an antimicrobial coating on a surface of a substrate, said method comprising:

condensing a carbonaceous vapor consisting essentially of carbonaceous precursor material onto said surface under condensing conditions effective to induce the formation of covalent bonds between substrate atoms and carbon atoms in said carbonaceous vapor, producing a bonding region comprising hydrogenated amorphous carbon covalently bonded to said substrate;

exposing an antimicrobial metal to physical vapor deposition techniques, thereby producing a metallic stream consisting essentially of an antimicrobial metal selected from the group consisting of Ag, Au, Pt, Pd, Ir, Sn, Cu, Sb, Bi, Zn, and combinations thereof;

condensing a combination comprising said carbonaceous vapor and said metallic stream onto said hydrogenated amorphous carbon at a ratio and under incorporation conditions effective to produce an antimicrobial region comprising hydrogenated amorphous carbon having dispersed therein an antimicrobially effective load of antimicrobial metal ions, wherein said metallic stream is introduced at a varied rate and produces a gradient of said antimicrobial metal in said hydrogenated amorphous carbon.

55. The method of claim 52 wherein said gradient comprises from about 0.5 to about 1 mg/cm² based on surface area of said/antimicrobial coating.

56. The method of claim 55 wherein said varied rate is from about 0.5 Å/sec to about 10 Å/sec.

57. The method of claim 56 wherein said varied rate comprises an initial rate of from about 0.5 Å/sec to about 10 Å/sec; and a subsequent rate of from about 2 Å/sec to about 5 Å/sec.

58. The method of claim 52 wherein said initial rate and said subsequent rate each are maintained for about 15 minutes to about 30 minutes.

59. The method of claim 57 further comprising discontinuing said carbonaceous vapor to produce an antimicrobial coating comprising an outer surface consisting essentially, of said antimicrobial metal.

60. The method of claim 56 wherein
said condensation conditions comprise bombardment with a beam of ions at an condensation energy and amperage effective to induce said formation of covalent bonds and to convert said carbonaceous precursor material to said hydrogenated amorphous carbon; and
said incorporation conditions comprise bombardment with a beam of ions at an incorporation energy and amperage effective to convert said combination to hydrogenated amorphous carbon having dispersed therein an antimicrobially effective load of antimicrobial metal ions.

61. The method of claim 60 wherein both said condensation energy and amperage and said incorporation energy and amperage have the following values:
said energy is from about 1 to about 10 keV; and, said amperage is from about 10 to about 50 mA.

62. The method of claim 56 further comprising discontinuing said carbonaceous vapor to produce an antimicrobial coating comprising an outer surface consisting essentially of said antimicrobial metal.

63. The method of claim 55 wherein said varied rate comprises
an initial rate of from about 0.5 Å/sec to about 10 Å/sec; and
a subsequent rate of from about 2 Å/sec to about 5 Å/sec.

64. The method of claim 63 wherein said initial rate and said subsequent rate each are maintained for about 15 minutes to about 30 minutes.

65. The method of claim 64 wherein said initial rate and said subsequent rate each are maintained for about 15 minutes to about 30 minutes.

66. The method of claim 65 wherein
said condensation conditions comprise bombardment with a beam of ions at an condensation energy and amperage effective to induce said formation of covalent bonds and to convert said carbonaceous precursor material to said hydrogenated amorphous carbon; and
said incorporation conditions comprise bombardment with a beam of ions at an incorporation energy and amperage effective to convert said combination to hydrogenated amorphous carbon having dispersed therein an antimicrobially effective load of antimicrobial metal ions.

67. The method of claim 66 wherein both said condensation energy and amperage and said incorporation energy and amperage have the following values:
said energy is from about 1 to about 10 keV; and,
said amperage is from about 10 to about 50 mA.

68. The method of claim 67 further comprising discontinuing said carbonaceous vapor to produce an antimicrobial coating comprising an outer surface consisting essentially of said antimicrobial metal.

69. The method of claim 63 further comprising discontinuing said carbonaceous vapor to produce an antimicrobial coating comprising an outer surface consisting essentially of said antimicrobial metal.

70. The method of claim 55 further comprising discontinuing said carbonaceous vapor to produce an antimicrobial coating comprising an outer surface consisting essentially of said antimicrobial metal.

71. The method of claim 54 wherein said varied rate is from about 0.5 Å/sec to about 10 Å/sec.

72. The method of claim 71 wherein said varied rate comprises
an initial rate of from about 0.5 Å/sec to about 10 Å/sec; and
a subsequent rate of from about 2 Å/sec to about 5 Å/sec.

73. The method of claim 71 wherein said initial rate and said subsequent rate each are maintained for about 15 minutes to about 30 minutes.

74. The method of claim 54 wherein said varied rate comprises
an initial rate of from about 0.5 Å/sec to about 10 Å/sec; and
a subsequent rate of from about 2 Å/sec to about 5 Å/sec.

75. The method of claim 74 wherein said initial rate and said subsequent rate each are maintained for about 15 minutes to about 30 minutes.

76. The method of claim 75 wherein said initial rate and said subsequent rate each are maintained for about 15 minutes to about 30 minutes.

77. The method of claim 74 further comprising discontinuing said carbonaceous vapor to produce an antimicrobial coating comprising an outer surface consisting essentially of said antimicrobial metal.

78. The method of claim 54 wherein
said condensation conditions comprise bombardment with a beam of ions at an condensation energy and amperage effective to induce said formation of covalent bonds and to convert said carbonaceous precursor material to said hydrogenated amorphous carbon; and
said incorporation conditions comprise bombardment with a beam of ions at an incorporation energy and amperage effective to convert said combination to hydrogenated amorphous carbon having dispersed therein an antimicrobially effective load of antimicrobial metal ions.

79. The method of claim 78 wherein both said condensation energy and amperage and said incorporation energy and amperage have the following values:
said energy is from about 1 to about 10 keV; and,
said amperage is from about 10 to about 50 mA.

80. The method of claim 54 further comprising discontinuing said carbonaceous vapor to produce an antimicrobial coating comprising an outer surface consisting essential of said antimicrobial metal.

81. A method of forming an antimicrobial coating on a surface of a substrate, said method comprising:
condensing a carbonaceous vapor consisting essentially of carbonaceous precursor material onto said surface under condensing conditions effective to induce the formation of covalent bonds between substrate atoms and carbon atoms in said carbonaceous vapor, producing a bonding region comprising hydrogenated amorphous carbon covalently bonded to said substrate;
exposing silver to physical vapor deposition techniques, thereby producing a metallic stream consisting essentially of silver;
condensing a combination comprising said carbonaceous vapor and said metallic stream onto said hydrogenated amorphous carbon at a ratio and under incorporation conditions effective to produce an antimicrobial region comprising hydrogenated amorphous carbon having dispersed therein an antimicrobially effective amount of silver ions, wherein said metallic stream is introduced at a varied rate and produces a gradient of said antimicrobial metal in said hydrogenated amorphous carbon.

82. The method of claim 81 wherein said gradient comprises from about 0.5 to about 1 mg/cm$_2$ based on surface area of said antimicrobial coating.

83. The method of claim 82 wherein said varied rate is from about 0.5 Å/sec to about 10 Å/sec.

84. The method of claim 83 wherein said varied rate comprises an initial rate of from about 0.5 Å/sec to about 10 Å/sec; and a subsequent rate of from about 2 Å/sec to about 5 Å/sec.

85. The method of claim 84 wherein said initial rate and said subsequent rate each are maintained for about 15 minutes to about 30 minutes.

86. The method of claim 85 wherein said condensation conditions comprise bombardment with a beam of ions at an condensation energy and amperage effective to induce said formation of covalent bonds and to convert said carbonaceous precursor material to said hydrogenated amorphous carbon; and said incorporation conditions comprise bombardment with a beam of ions at an incorporation energy and amperage effective to convert said combination to hydrogenated amorphous carbon having dispersed therein an antimicrobially effective load of antimicrobial metal ions.

87. The method of claim 86 wherein both said condensation energy and amperage and said incorporation energy and amperage have the following values:

said energy is from about 1 to about 10 keV; and, said amperage is from about 10 to about 50 mA.

88. The method of claim 82 wherein said varied rate comprises an initial rate of from about 0.5 Å/sec to about 10 Å/sec; and a subsequent rate of from about 2 Å/sec to about 5 Å/sec.

89. The method of claim 88 wherein said initial rate and said subsequent rate each are maintained for about 15 minutes to about 30 minutes.

90. The method of claim 81 wherein said varied rate is from about 0.5 Å/sec to about 1 Å/sec.

91. The method of claim 90 wherein said varied rate comprises an initial rate of from about 0.5 Å/sec to about 10 Å/sec; and a subsequent rate of from about 2 Å/sec to about 5 Å/sec.

92. The method of claim 91 wherein said initial rate and said subsequent rate each are maintained for about 15 minutes to about 30 minutes.

93. The method of claim 81 wherein said varied rate comprises an initial rate of from about 0.5 Å/sec to about 10 Å/sec; and a subsequent rate of from about 2 Å/sec to about 5 Å/sec.

94. The method of claim 93 wherein said initial rate and said subsequent rate each are maintained for about 15 minutes to about 30 minutes.

95. The method of claim 81 wherein said condensation conditions comprise bombardment with a beam of ions at an condensation energy and amperage effective to induce said formation of covalent bonds and to convert said carbonaceous precursor material to said hydrogenated amorphous carbon; and said incorporation conditions comprise bombardment with a beam of ions at an incorporation energy and amperage effective to convert said combination to hydrogenated amorphous carbon having dispersed therein an antimicrobially effective load of antimicrobial metal ions.

96. The method of claim 95 wherein both said condensation energy and amperage and said incorporation energy and amperage have the following values:

said energy is from about 1 to about 10 keV; and, said amperage is from about 10 to about 50 mA.

97. A method of forming an antimicrobial coating on a surface of a substrate, said method comprising:

condensing a carbonaceous vapor consisting essentially of carbonaceous precursor material onto said surface under condensing conditions effective to induce the formation of covalent bonds between atoms of said substrate and carbon atoms in said carbonaceous vapor, producing a bonding region comprising hydrogenated amorphous carbon covalently bonded to said substrate;

exposing an antimicrobial metal to physical vapor deposition techniques, thereby producing a metallic stream consisting essentially of an antimicrobial metal selected from the group consisting of Ag, Au, and combinations thereof;

condensing a combination comprising said carbonaceous vapor and said metallic stream onto said hydrogenated amorphous carbon at a ratio and under incorporation conditions effective to produce an antimicrobial region comprising hydrogenated amorphous carbon having, dispersed therein an antimicrobially effective load of antimicrobial metal ions, wherein said metallic stream is introduced at a varied rate and produces a gradient of said antimicrobial metal in said hydrogenated amorphous carbon.

98. The method of claim 97 wherein said gradient comprises from about 0.5 to about 1 mg/cm$^2$ based on surface area of antimicrobial coating.

99. The method of claim 98 wherein said varied rate is from about 0.5 Å/sec to about 10 Å/sec.

100. The method of claim 99 wherein said varied rate comprises an initial rate of from about 0.5 Å/sec to about 10 Å/sec; and a subsequent rate of from about 2 Å/sec to about 5 Å/sec.

101. The method of claim 100 wherein said initial rate and said subsequent rate each are maintained for about 15 minutes to about 30 minutes.

102. The method of claim 101 wherein said condensation conditions comprise bombardment with a beam of ions at an condensation energy and amperage effective to induce said formation of covalent bonds and to convert said carbonaceous precursor material to said hydrogenated amorphous carbon; and said incorporation conditions comprise bombardment with a beam of ions at an incorporation energy and amperage effective to convert said combination to hydrogenated amorphous carbon having dispersed therein an antimicrobially effective load of antimicrobial metal ions.

103. The method of claim 102 wherein both said condensation energy and amperage and said incorporation energy and amperage have the following values:

said energy is from about 1 to about 10 keV; and, said amperage is from about 10 to about 50 mA.

104. The method of claim 103 further comprising discontinuing said carbonaceous vapor to produce an antimicrobial coating comprising an outer surface consisting essentially of said antimicrobial metal.

105. The method of claim 101 further comprising discontinuing said carbonaceous vapor to produce an antimicrobial coating comprising an outer surface consisting essentially of said antimicrobial metal.

106. The method of claim 100 further comprising discontinuing said carbonaceous vapor to produce an antimicrobial coating comprising an outer surface consisting essentially of said antimicrobial metal.

107. The method of claim 99 further comprising discontinuing said carbonaceous vapor to produce an antimicrobial coating comprising an outer surface consisting essentially of said antimicrobial metal.

108. The method of claim 98 wherein said varied rate comprises an initial rate of from about 0.5 Å/sec to about 10 Å/sec; and a subsequent rate of from about 2 Å/sec to about 5 Å/sec.

109. The method of claim 108 wherein said initial rate and said subsequent rate each are maintained for about 15 minutes to about 30 minutes.

110. The method of claim 98 further comprising discontinuing said carbonaceous vapor to produce an antimicrobial coating comprising an outer surface consisting essentially of said antimicrobial metal.

111. The method of claim 97 wherein said varied rate is from about 0.5 Å/sec to about 10 Å/sec.

112. The method of claim 111 further comprising discontinuing said carbonaceous vapor to produce an antimicrobial coating comprising an outer surface consisting essentially of said antimicrobial metal.

113. The method of claim 97 wherein said varied rate comprises an initial rate of from about 0.5 Å/sec to about 10 Å/sec; and a subsequent rate of from about 2 Å/sec to about 5 Å/sec.

114. The method of claim 113 wherein said initial rate and said subsequent rate each are maintained for about 15 minutes to about 30 minutes.

115. The method of claim 114 further comprising discontinuing said carbonaceous vapor to produce an antimicrobial coating comprising an outer surface consisting essentially of said antimicrobial metal.

116. The method of claim 113 further comprising discontinuing said carbonaceous vapor to produce an antimicrobial coating comprising an outer surface consisting essentially of said antimicrobial metal.

117. The method of claim 97 wherein said condensation conditions comprise bombardment with a beam of ions at an condensation energy and amperage effective to induce said formation of covalent bonds and to convert said carbonaceous precursor material to said hydrogenated amorphous carbon; and said incorporation conditions comprise bombardment with a beam of ions at an incorporation energy and amperage effective to convert said combination to hydrogenated amorphous carbon having dispersed therein an antimicrobially effective load of antimicrobial metal ions.

118. The method of claim 117 wherein both said condensation energy and amperage and said incorporation energy and amperage have the following values:

said energy is from about 1 to about 10 keV; and, said amperage is from about 10 to about 5 mA.

119. The method of claim 97 further comprising discontinuing said carbonaceous vapor to produce an antimicrobial coating comprising an outer surface consisting essentially of said antimicrobial metal.

* * * * *